April 28, 1936. S. M. PAGE Plant Pat. 176
POINSETTIA
Filed May 16, 1935
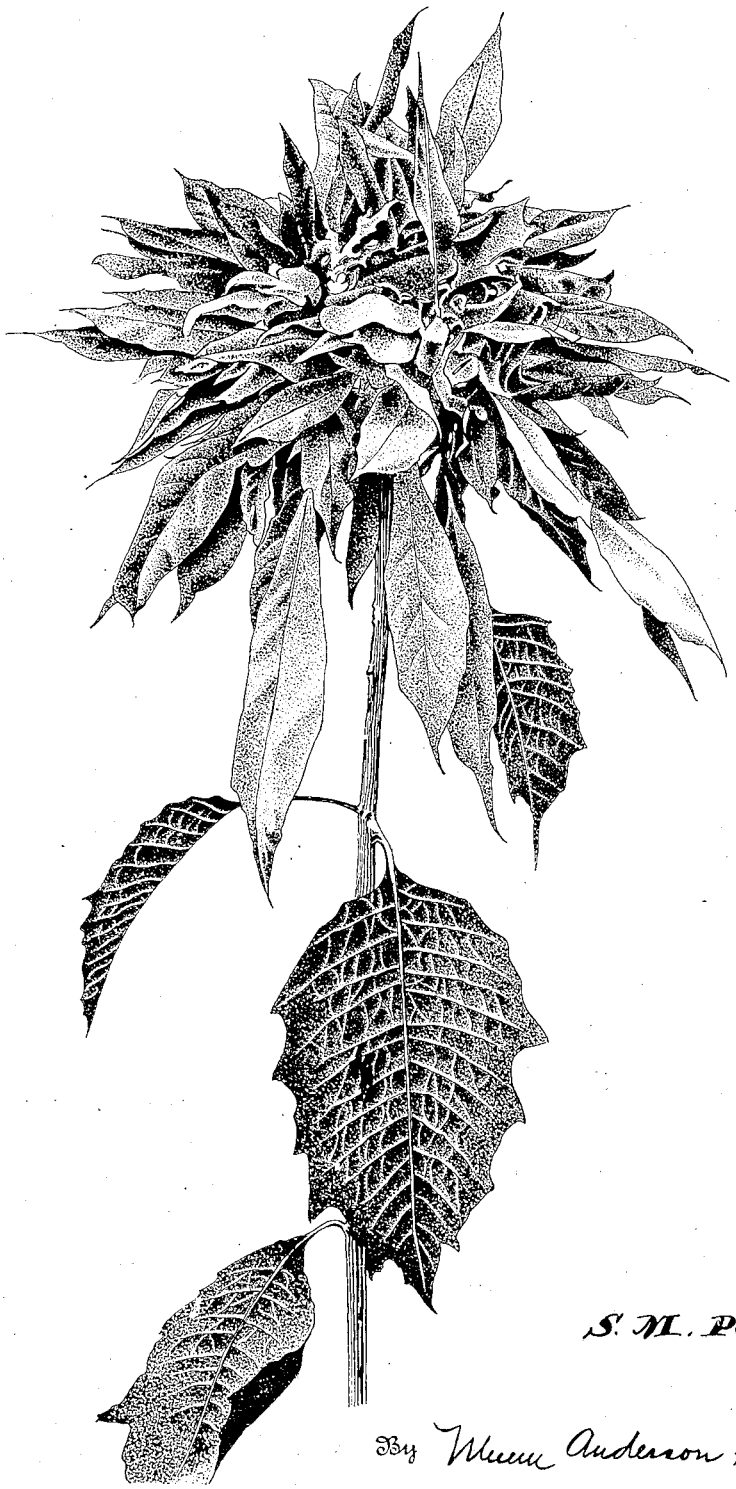
Inventor
S. M. Page.
By Wm. Anderson & Kiddy
Attorneys Patented Apr. 28, 1936

Plant Pat. 176

UNITED STATES PATENT OFFICE

176

POINSETTIA

Stephen M. Page, Port Arthur, Tex.

Application May 16, 1935, Serial No. 21,871

1 Claim. (Cl. 47—59)

My invention relates to improvements in poinsettias of the kind which is commonly known as the "oak leaf" type. The principal novel characteristic of the new poinsettia is the multiplicity of bracts as compared with the ordinary variety.

The plant has, however, in addition to this feature, other novel characteristics, which will be described in the following specification and set forth in the appended claim.

The plant is illustrated in the accompanying drawing which shows the mass of bracts that gives to the plant its novel aspect.

The plant was produced by taking cuttings from the parent plant and by careful selection and continued cutting from year to year until the plant, as set forth in the accompanying drawing, was perfected.

The plant has from three hundred to four hundred bracts to each bloom, and, as shown by the drawing, these bracts are in a compact arrangement which makes them stand out in all directions. The color is of a vivid red, making it strikingly beautiful.

One novel characteristic of this plant, although it is not the main distinguishing characteristic, is that it is a slow grower, being from twenty-five to thirty-five percent slower than those of other types. The foliage is light green in color, long and broad. The edges are slightly scalloped like the oak leaf type and are very thick and heavily veined. The foliage is also tough and the leaves hold onto the stem tenaciously under various conditions.

The following is a summary of the descriptive characteristics of this new poinsettia:—

*Parentage*

Common oak leaf poinsettia.

*Cluster of bracts*

*Size.*—Very large.
*Form.*—Full.
*Lasting quality.*—Very good, about sixty days.

*Fragrance*

None.

*Blooms borne*

The blooms are borne in small clusters, one cluster to a stem about which the cluster of bracts develops.

*Petalage*

The number of bracts about the flower cluster is greatly increased.

*Color*

Vivid red corresponding to that given by Maerz and Paul's Dictionary of color, Plate 3, row 6, column K, designated "Hockey".

*Foliage*

*Quantity.*—Normal.
*Color.*—Light green.
*Texture.*—Leathery.
*Size.*—Very large.
*Growth.*—Moderate.
*Habit.*—Upright.

*Blooming*

One season of blooming—December. One flower cluster with its accompanying bracts at the end of each branch.

It is to be understood that the foregoing characteristics are typical, but may be subject to slight variation in different environments.

What I claim as new is:

The poinsettia herein shown and described, characteristized particularly by: very greatly increased number of bracts about the cluster of flowers, said bracts having very long lasting quality; relatively slow growth of the plant; large thick tough leaves clinging tenaciously to the stem.

STEPHEN M. PAGE.